(12) United States Patent
Sasahara et al.

(10) Patent No.: US 8,541,020 B2
(45) Date of Patent: Sep. 24, 2013

(54) POLYMERIC HYDROGEL

(75) Inventors: Shuichi Sasahara, Nara (JP); Kazuhiro Yosikawa, Nara (JP); Shinichi Wakamatsu, Nara (JP); Takahiko Fujita, Nara (JP)

(73) Assignee: Seikisui Plastics Co., Ltd., Osaka (JP)

( * ) Notice: Subject to any disclaimer, the term of this patent is extended or adjusted under 35 U.S.C. 154(b) by 637 days.

(21) Appl. No.: 10/485,829

(22) PCT Filed: Sep. 17, 2002

(86) PCT No.: PCT/JP02/09533
§ 371 (c)(1),
(2), (4) Date: Feb. 19, 2004

(87) PCT Pub. No.: WO03/025062
PCT Pub. Date: Mar. 27, 2003

(65) Prior Publication Data
US 2004/0191316 A1    Sep. 30, 2004

(30) Foreign Application Priority Data
Sep. 18, 2001  (JP) .................... 2001-283832

(51) Int. Cl.
*A61F 13/00*    (2006.01)
(52) U.S. Cl.
USPC ............ 424/443; 424/78.17; 424/78.18; 424/78.08; 600/395
(58) Field of Classification Search
USPC ............ 424/443; 204/414, 418; 528/317
See application file for complete search history.

(56) References Cited

U.S. PATENT DOCUMENTS

| | | | |
|---|---|---|---|
| 5,278,206 A | | 1/1994 | Göbel et al. |
| 5,421,982 A | * | 6/1995 | Ikeda et al. ............ 204/403.02 |
| 6,005,126 A | * | 12/1999 | Ishitobi et al. ............ 554/227 |
| 2002/0015714 A1 | * | 2/2002 | Agostini et al. ............ 424/401 |

FOREIGN PATENT DOCUMENTS

| | | | | |
|---|---|---|---|---|
| EP | 0940148 | | 9/1999 | |
| JP | 63311960 A | * | 12/1988 | .............. 424/77 |
| JP | 4-503222 | | 6/1992 | |
| JP | 5-320612 | | 3/1993 | |
| JP | 08-182659 | * | 12/1994 | ............ 204/403.02 |
| JP | 8-182659 | | 7/1996 | |
| JP | 10-95962 | | 4/1998 | |
| JP | 2803886 | | 7/1998 | |
| JP | 11-209222 | * | 3/1999 | |
| JP | 11-209222 | | 8/1999 | |
| JP | 11279288 | | 10/1999 | |
| JP | 11315148 | | 11/1999 | |
| JP | 11349786 | | 12/1999 | |
| JP | 2001-406 | | 1/2001 | |

OTHER PUBLICATIONS

English Language Abstract of JP 5-320612, 2006.
English Language Abstract of JP 11-20922, 2006.
English Language Abstract of JP-8-182659, 2004.
English Language Abstract of JP-2001-406, 2004.
English Language Abstract of JP 2803886, 2004.
English Language Abstract of JP-11-349786, 2004.
English Language Abstract of JP4-503222, 2004.
English Language Abstract of 11-315148, 2004.
English Language Abstract of 11-279288, 2004.
English Language Abstract of 10-95962, 2004.

* cited by examiner

*Primary Examiner* — James Rogers
(74) *Attorney, Agent, or Firm* — Greenblum & Bernstein P.L.C.

(57) ABSTRACT

The invention aims at providing a polymeric hydrogel which is highly resistant to water washing.

The aim is attained by a polymeric hydrogel comprising a polymeric matrix formed by copolymerizing a nonionic polymerizable monomer with a crosslinking monomer, characterized in that the polymeric matrix contains a wetting agent and water, at least 50 wt % of the wetting agent is constituted of a polymer prepared by polymerizing a polyhydric alcohol monomer component containing a trihydric or more alcohol monomer, and the polymer is a water-soluble one which has an average molecular weight of 150 to 4000 and satisfies the relationship: {(number of ether groups in the polymer+number of hydroxyl groups in the polymer)/number of carbon atoms present in the polymer}≧1/3.

7 Claims, 2 Drawing Sheets

POLYMERIC HYDROGEL

TECHNICAL FIELD

The present invention relates a polymeric hydrogel. The polymeric hydrogel of the present invention can be suitably used as materials of bioelectrodes, medical adhesives, coupling materials for ultrasonic measuring, cosmetics, quasi-drugs, electrodes for industrial measurements and industrial adhesives.

CONVENTIONAL ART

Polymeric hydrogels contained polymeric matrixes comprising crosslinked polymers with wetting agents and water are utilized in various fields. For example, as bioelectrodes, there have been conventionally used conductive polymeric hydrogels which contain polymeric matrixes formed by crosslinking electrolytic polymers such as polyacrylic acid and the like with wetting agents and water. In a polymeric hydrogel, since:a polymeric matrix is hydrophilic, and has permeability of water and contains water, it is easy to add an electrolyte and in addition it is possible to lower impedance. Therefore, it exerts adequate performance as an electrode for highly accurate measurement such as monitoring of an electrocardiogram.

When the above-mentioned conductive polymeric hydrogel was used once by being stuck to the surface of a living body, it was commonly disposable because sticking force was deteriorated due to the adhesion of sebum and keratins of the surface of skin to the surface of gel. But, since it is economically disadvantageous to use the gel only once and to dispose of the gel, a reusable bioelectrode was desired and such an electrode was reported in Japanese Unexamined Patent Publication No. HEI 8(1996)-182659. However, even the electrode of the above-mentioned patent publication could not prevent the sticking force from being deteriorated every time the electrode is used and satisfactory reusability could not be attained. Further, polymeric hydrogels had little water resistance and had defects of being hard to water wash since polymeric matrixes are hydrophilic and, simultaneously, components included in gels are also hydrophilic.

As the method of solving a problem of reuse, methods of using an oleophilic gel existing conventionally, silicone gel and polyurethane are conceivable. These oleophilic gel, silicone gel and polyurethane are low in hydrophilicity and have physicochemical properties withstanding water washing. However, when these were applied to living bodies, these caused contact dermatitis due to a steamy condition since these had extremely low permeability of water and these were not suitable for applications requiring electrical conductivities, particularly, highly accurate electrical measurement such as monitoring of an electrocardiogram since an amount of electrolyte, which can be added to the gel, is extremely small.

In order to solve this problem, a conductive polymeric gel, which is water-washable, is reported in Japanese Unexamined Patent Publication No. 2001-406. This conductive polymeric gel is a hydrogel containing water and polyhydric alcohol and, also, is characterized by being capable of recovering an initial sticking force by water washing the surface of the conductive polymeric gel to remove stains.

However, even in the conductive polymeric gel of the above-mentioned patent publication, it is a reality that the polyhydric alcohol contained in the gel is eluted gradually as the gel is water washed repeatedly and therefore, that the gel's ability to retain water is gradually deteriorated and, simultaneously, its flexibility and sticking force are also deteriorated.

DISCLOSURE OF THE INVENTION

The present inventors conducted studies earnestly with the aim of developing a polymeric hydrogel which is significantly low in deterioration of physical properties represented by sticking force even when the polymeric hydrogel is water-washed repeatedly and, consequently, have reached to complete the present invention.

Thus, according to the present invention, there is provided a polymeric hydrogel comprising a polymeric matrix formed by copolymerizing a nonionic polymerizable monomer with a crosslinking monomer, characterized in that the polymeric matrix contains a wetting agent and water, at least 50 wt % of the wetting agent is constituted of a polymer prepared by polymerizing a polyhydric alcohol monomer component containing a trihydric or more alcohol monomer, and the polymer is a water-soluble one which has an average molecular weight of 150 to 4000 and satisfies the relationship: {(number of ether groups in the polymer+number of hydroxyl groups in the polymer)/number of carbon atoms present in the polymer}$\geq 1/3$.

Further, according to the present invention, there is provided a polymeric hydrogel comprising a polymeric matrix formed by copolymerizing a nonionic polymerizable monomer with a crosslinking monomer, characterized in that the polymeric matrix contains a wetting agent containing at least 50 wt % of a polymer prepared by polymerizing a polyhydric alcohol monomer component, and water, and the polymeric hydrogel has an increase in the weight of gel relative to its own weight before immersion in water-immersing for 5 minutes is 50 wt % or less and a decrease in the weight of gel relative to its own weight before immersion in water-immersing for 5 minutes and then drying is 10 wt % or less.

MODE FOR CARRYING OUT THE INVENTION

Figure 1:
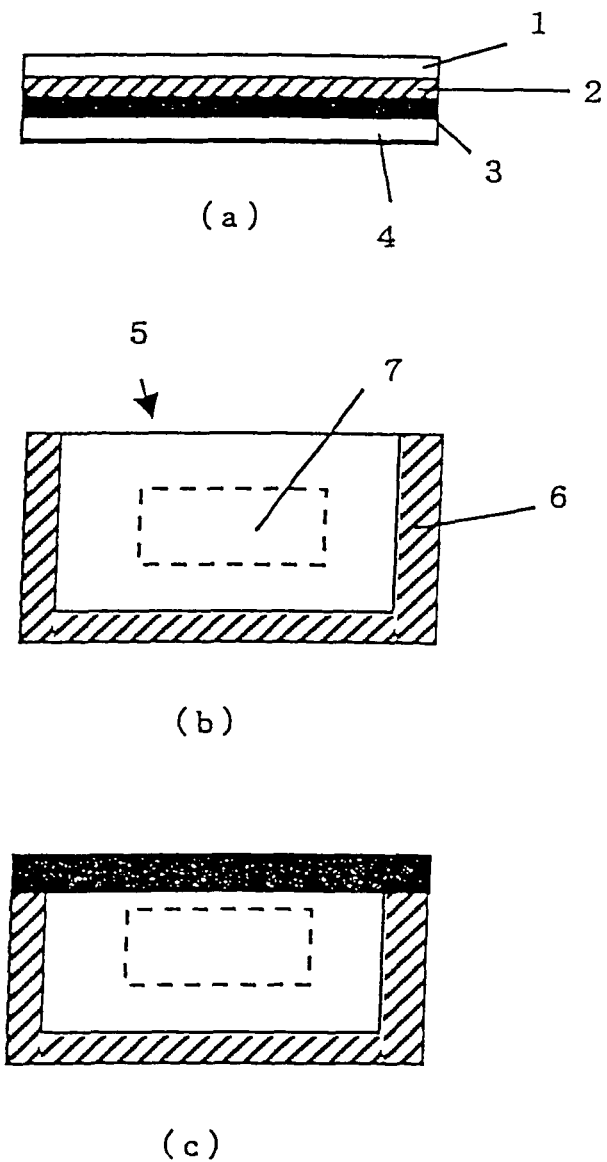
FIG. 1 is a schematic view showing one example of a method of holding the polymeric hydrogel of the present invention.

A nonionic polymerizable monomer capable of being used in the present invention is not specifically limited as long as it has a nonionic property. Herein, as the nonionic polymerizable monomer, a monomer, 1 wt % water solution of which exhibits a pH of 4 to 9, is preferably used, and a monomer exhibiting a pH of 6 to 8 is more preferable. Specifically, examples thereof include: esters of acrylic acid such as (poly)ethyleneglycol (meth)acrylate, (poly)propyleneglycol (meth)acrylate, and (poly)glycerin (meth)acrylate; (meth)acrylamides; and N-substituted (meth)acrylamides such as N-methyl(meth)acrylamide, N-ethyl(meth)acrylamide, N-propyl(meth)acrylamide, N-butyl(meth)acrylamide, and N,N-dimethyl(meth)acrylamide, diacetoneacrylamide; and N-vinylamide derivatives such as N-vinylpyrrolidone, N-vinylformamide, and N-vinylacetoamide, and these compounds may be used alone or as a combination of two or more kinds. Here, in the above exemplification and the following exemplification, the term "(meth)acryl" means acryl or methacryl.

Here, in a polymeric matrix produced by using an ionic polymerizable monomer, an ionic group of a side chain is ionized in a polymeric hydrogel and, therefore, the polymeric matrix is in a condition of being either positively or negatively charged. Therefore, each straight chain of the polymeric matrix always has a property of repelling each other always, and when a large amount of water contacts these straight chains, a network of the polymeric matrix is broadened in a short time and the polymeic matrix exerts larger water absorbing capacity. This means that a change in the gel is large and, consequently, the stability of the gel becomes low.

On the other hand, since a nonionic polymerizable monomer is used in the present invention, such a change is less. In addition, when the ionic group is not present in the polymeric matrix, the polymeric matrix is insensitive to electricity upon electrical measurement and medical treatment. That is, since electrical repulsion at an interface between the element of an electrode and the polymeric hydrogel become resistant to develop and, also, a shrinkage of gel due to the addition of electrolyte for imparting conductivity to the gel is resistant to develop, the gel of the present invention can become a high-performance conductive polymeric hydrogel. Further, when a polymeric hydrogel containing medicinal ingredients and various additives is produced, for example, even in the case where medicinal ingredients are electrolytes, this polymeric hydrogel does not generate an interaction between the ionic group in the polymerizable monomer and the medicinal ingredients and has an advantage that the addition of the medicinal ingredients is easy.

On the other hand, as a crosslinking monomer, a monomer having two or more double bonds having a polymerizable property in a molecule is preferably used. Specifically, examples thereof include polyfunctional (meth)acrylamides such as methylenebis(meth)acrylamide, ethylenebis(meth)acrylamide, (poly)ethyleneglycol di(meth)acrylate, (poly)propyleneglycol di(meth)acrylate, glycerin di(meth)acrylate, and glycerin tri(meth)acrylate, or (meth)acrylate, tetraaryloxy ethane, or diaryl ammonium chloride, and these compounds may be used alone or as a combination of two or more kinds. Herein, since the crosslinking monomer may be used in a less amount for the nonionic polymerizable monomer, either an ionic monomer or a nonionic monomer may be used, but the nonionic monomer is more preferred.

In addition, as the above-mentioned crosslinking monomer having two or more double bonds having a polymerizable property in a molecule, there can be used polyglycerin derivatives, being polyfunctional compounds having two or more (meth)acryloyl groups or vinyl groups and having a molecular weight of 400 or higher, described in Japanese Patent Publication 2803886.

An increase in weight by water-absorbing becomes large as an water immersion time of the polymeric hydrogel becomes long and, normally, reaches equilibrium in several hours to about 24 hours, at latest about 48 hours. As described above, the gel having an affinity for water generally absorbs not a little water and increases in volume together with an increase in weight. Therefore, there is a possibility that the material destruction of gel itself may occur and, in a product configuration of gel combined with a supporting base, there is a possibility of causing a problem of peeling off and falling off from the supporting base. Further, in the gel having expanded in volume, a network of the polymeric matrix is expanded and the ability of the gel to retain components included is significantly deteriorated, and finally there is a possibility that components included is eluted out of the gel.

However, actually, when the gel to be used is one having an area of, for example, about 50 cm$^2$, stains of a surface can be removed by water washing for several seconds and the prolonged immersion described above is not necessary. The present inventors have found that in a polymeric hydrogel, preferably, an increase in the weight of gel relative to its own weight before immersion in water-immersing for 5 minutes is 50 wt % or less of its own weight and a decrease in the weight of gel relative to its own weight before immersion in water-immersing for 5 minutes and drying is 10 wt % or less in order to realize that physical properties of gel is not impaired even when water washing of the period of several seconds described above is repeated.

That an increase in the weight of gel relative to its own weight before immersion in water-immersing the polymeric hydrogel for 5 minutes is 50 wt % or less means that an increment of the weight of gel, which occurs when the polymeric hydrogel is immersed in ion-exchanged water for 5 minutes to absorb water, is 50 wt % or less of its own weight before immersion, and this relationship is expressed by the following equation. Here, the polymeric hydrogel before immersion represents one having an amount of water reaching equilibrium.

Increase in the weight upon immersion of the period of 5 minutes=(gel weight after immersion−gel weight before immersion)/gel weight before immersion≦0.5 . . . Equation 1

In addition, due to water-absorbing, the gel increases in weight and, simultaneously, a network of the polymeric matrix is expanded and a part of components included is eluted. That a decrease in the weight of gel relative to its own weight before immersion in water-immersing for 5 minutes and drying the polymeric hydrogel is 10 wt % or less means that an amount of a wetting agent or the like, being a part of components included, which are diffused or eluted from the gel having expanded in volume and in the network of the polymeric matrix due to water immersion of the period of 5 minutes into water in which the gel is immersed, is 10 wt % or less of the gel weight before immersion.

Examples of the polymer, which can be used to the present invention, prepared by polymerizing a polyhydric alcohol monomer component include a water-soluble (term "water-soluble" means that 10 g or more can be dissolved in 100 g of water) polymer of one kind, or two or more kinds of ethylene glycol, propylene glycol, butanediol, pentanediol, glycerin, pentaerythritol, sorbitol, sorbitan or saccharide.

The polymer prepared by polymerizing a polyhydric alcohol monomer component is desirably liquid at room temperature (about 25° C.) in point of the viscoelasticity characteristic of gel and in point of a handling property in producing. In addition, the above polymer may have a functional group such as an ester bond, an aldehyde group, or a carboxyl group in a molecule or at an end of the repeating unit.

Further as the polymer prepared by polymerizing a polyhydric alcohol monomer component, there can be used a polymer which comprises a polymer formed by polymerizing a polyhydric alcohol monomer component containing a trihydric or more alcohol monomer and in which the polymer formed by polymerization has the relationship: {(number of ether groups present in the polymer+number of hydroxyl groups present in the polymer)/number of carbon atoms present in the polymer}≧1/3. In addition, when this polymer is used, there may be cases where a polymeric hydrogel withstanding a practical use can be provided in some applications even though an increase in the weight of gel relative to its own weight before immersion in water-immersing for 5 minutes is larger than 50 wt % of its own weight and/or a decrease in the weight of gel relative to its own weight before immersion in water-immersing for 5 minutes and drying the polymeric hydrogel is larger than 10 wt %.

In addition, by locating a unit derived from the trihydric or more alcohol monomers in a repeating unit of a polymer, a wetting function as the wetting agent is improved and, also, electrostatic interactions with a polymeric matrix and a solvent are enhanced; therefore, the elution of a wetting agent from the inside of gel can be more reduced. Even when a unit derived from these monomers is located in only a part of the polymer, it is possible to make the polymer in liquid form even if a molecular weight of polymer is high since the crystallinity of polymer can be reduced. Incidentally, a hydroxyl group not polymerized may remain in the trihydric or more alcohol monomer unit. When the units derived from the trihydric or more alcohol monomers are present, a wetting performance can be improved since the unreacted hydroxyl group can remain in the polymer.

Though the number of hydroxyl groups contained in the polyhydric alcohol is not specifically limited, it is preferred to have six or more hydroxyl groups in a polymer molecule to attain good ability to retain moisture. In addition, when the number of these hydroxyl groups exceeds 12, this is not preferable since association of polymers with each other is promoted to increase viscosity significantly and the handling property becomes poor. Incidentally, the number of hydroxyl groups, described herein, is derived from a polymerization degree determined based on the average molecular weight of polymer. For example, in the case of polyglycerin which is prepared by polymerizing glycerin as a trihydric or more alcohol, when it is a tetramer, the number of hydroxyl groups in a molecule is 6 and when it is a decamer, the number of hydroxyl groups in a molecule is 12.

An example of the above-mentioned polymer prepared by polymerizing a polyhydric alcohol monomer component containing a trihydric or more alcohol monomer includes a polymer prepared by polymerizing a monomer containing at least a trihydric or more alcohol monomer in a molecule such as glycerin, pentaerythritol, sorbitol, sorbitan and saccharide (for example, monosaccharide such as glucose and fructose, and disaccharose such as sucrose and lactose).

Preferably, the polymer prepared by polymerizing these monomers containing a trihydric or more alcohol monomer in a molecule is also liquid at room temperature. For example, a polyglycerin prepared by polymerizing glycerin being liquid at room temperature alone is excellent in a handling property since it is liquid at room temperature. A monomer, which is solid at room temperature, such as sorbitol and sucrose can be converted to a liquid monomer by copolymerizing in combination of different monomers or by grafting liquid polymers like polyglycerin.

An average molecular weight of the polymer, prepared by polymerizing a polyhydric alcohol monomer component containing a trihydric or more alcohol monomer, is preferably 150 to 4000 though this varies depending on the kinds of monomers constituting a polymer, and more preferably 300 to 4000. In this specification, an average molecular weight means a number-average molecular weight measured with GPC (Gel Permeation Chromatography).

When the wetting agent is a polyhydric alcohol monomer component having a low molecular weight, or a polymer which is obtained by polymerizing the polyhydric alcohol monomer component but has an average molecular weight of less than 150, it is prone to be released from restraint of the network to be eluted when the gel absorbs water and the network of the polymeric matrix is broadened. The reason for this is that since these are compounds of a low molecular weight, which has small steric hindrance, these are hydrogen-bonded to the polymeric matrix and stabilized when the gel reaches equilibrium, but since it has small steric hindrance, water tends to cut in the hydrogen bond to occur hydration in absorbing water, and as a result, these are prone to be released from restraint of the network.

On the contrary, when the average molecular weight exceeds 4000, for example, even in the case where these polymers are liquid, polymer's viscosity is too high and, therefore, if the polymers are diluted using water or a polymerizable liquid monomer, the viscosity of a compound solution to be a raw material of gel is not sufficiently reduced. Accordingly, the handling property of the polymer becomes poor and, also, air bubbles are immixed in gel upon formation of the polymer into gel and deaerating operation may become difficult. In addition, when these polymers are solid, it takes much time to dissolve them and the viscosity of the resulting compound solution is also high and there is a possibility of causing the same detriment as that described above.

Even in polyhydric alcohol monomer component, there is one having a molecular weight of 150 or higher. For example, monosaccharide such as glucose, disaccharose such as sucrose, and further sorbitol correspond to this. Though these polyhydric alcohols have a measure of high molecular weight even in the case of monomer, they are poor in the ability to retain water and it is difficult to attain the gel having secular stability, for example, in the case of sucrose (molecular weight: 342).

The hydrogel has a good viscoelasticity characteristic by containing plasticizing components such as a wetting agent and water in a polymeric matrix. However, when the wetting agent of plasticizing components is solid at room temperature, water in gel solely has a function as the plasticizing components since the wetting agent itself does not have the function as the plasticizing components. The polyhydric alcohol monomer component having a high molecular weight, described above, is solid at room temperature and does not have the function as the plasticizer. When such a monomer is used, a large amount of water is required to dissolve the monomer also in preparing the compound solution, and it is difficult to heat and dissolve a monomer since the monomer has high crystallinity and a high melting point (for example, even in sorbitol, a melting point is 90° C. to 140° C.), and therefore the production of the gel is difficult.

Further, though the polyhydric alcohol monomer component may also be used in a part of the wetting agent, the amount of the polyhydric alcohol monomer component to be used is preferably limited to less than 50 wt % relative to the total amount of the wetting agent in order to reduce bad effects on the elution of wetting agent in absorbing water. When the amount of the polyhydric alcohol monomer component to be used is 50 wt % or less, the amount of elution of the wetting agent in absorbing water increases because the ratio of the polyhydric alcohol monomer component of a low molecular weight to the total amount of the wetting agent becomes large. In addition, the polyhydric alcohol monomer component and a simple polymer such as polyethyleneglycol may be used in combination to the extent not exceeding the above-mentioned range.

Preferably, the concentration of the polymeric matrix contained in the polymeric hydrogel in the present invention is 5 to 50 wt %, and more preferably, it is set at 5 to 40 wt %. The reason for this is that if the concentration is less than 5 wt %, since the concentration of the resulting gel matrix is too low, the solvent cannot be adequately retained and tends to bleed;

therefore, there is a possibility that the gel may become weak in hardness. On the other hand, in the polymeric hydrogel in which the polymeric matrix is produced in the concentration of higher than 50 wt %, since heat liberation in polymerization becomes too large, there is a possibility of boiling beyond a boiling point of a solvent. Further, when the solvent come to the boil, it becomes difficult to attain a good gel since air bubbles are immixed in the gel.

An amount of the crosslinking monomer to be added is preferably 0.05 to 10 wt % relative to the total amount of the polymeric matrix. When the addition amount is less than 0.05 wt %, the stability of shape becomes poor since a crosslinking density is low and, also, there is a possibility that a water-absorbing power becomes high because the distance between bridgings of the network becomes large and expansion of the network in absorbing water become large. When the amount of crosslinking monomer used exceeds 10 wt %, the resulting gel may become hard and brittle. In addition, the polymeric matrix described herein means a matrix formed by crosslinking between a polymerizable monomer and a crosslinking monomer.

Preferably, the concentration of the wetting agent in the polymeric hydrogel is 10 to 80 wt %, and more preferably, it is set at 20 to 70 wt %. When the concentration is less than 10 wt %, it is not preferable since the wetting power of gel is poor, the transpiration of water increases, the secular stability and the flexibility of gel are insufficient and it is often difficult to provide adhesion even in the case of requiring adhesion. When the concentration exceeds 80 wt %, it is not preferable since the concentrations of the polymeric matrix and water become low relatively. Further, this case is not preferable because when a monomer compound solution, including a polymerizable monomer, a crosslinking monomer, a wetting agent and water, is prepared, polymer's viscosity becomes too high and therefore the handling property of the polymer becomes poor, and also air bubbles are immixed in gel in forming the polymer into gel and deaerating operation becomes difficult.

In order to attain the polymeric hydrogel of the present invention, the crosslinking monomer in an amount of 0.05 to 10 wt % relative to the total amount of the polymeric matrix is preferably used, and the amount of polymeric matrix is suitable in a range from 5 to 50 wt % of the amount of gel. Therefore, the total amount of crosslinking monomer is preferably at most 5 wt % of the whole gel. The wetting agent is preferably used in an amount of 10 wt % or higher of the whole gel in order to exert its effects. Further, the polymer prepared by polymerizing a polyhydric alcohol monomer component is preferably used in the wetting agent in an amount of 50 wt % or higher of the wetting agent, i.e., 5 wt % or higher of the gel.

It is noted that since the above-mentioned polyglycerin derivatives as the polyfunctional compounds having (meth) acryloyl groups or vinyl groups and having a molecular weight of 400 or higher is difficult to be used in a sufficient amount for obtaining the polymeric hydrogel, it is not preferred.

In addition, the content of water contained in the hydrogel is preferably 5 to 50 wt %, more preferably 5 to 40 wt %. When the concentration is less than 5 wt %, since the water content of the gel relative to the water content in equilibrium is low, there is a possibility that a tendency of absorbing water in conducting water-washing is strengthened due to the increased hygroscopicity. In addition, when the content exceeds 50 wt %, since the deviation of the water content of the polymeric hydrogel from the water content in equilibrium becomes large, there is a possibility that a shrinkage of gel and a change in physical properties associated with drying become large.

The polymeric hydrogel may contain an electrolyte comprising salt. The amount of the electrolyte is preferably 13 wt % or lower relative to the amount of water contained in the hydrogel, more preferably 10 wt % or lower. When the concentration exceeds 13 wt %, there are cases where a crystal is precipitated in the gel or the dissolution of another components is inhibited since the dissolution of salt becomes difficult. In addition, a relatively large amount of salt is added in some cases when electrical conduction performance is required but addition of salt exceeding substantially 13 wt % is not preferred from the viewpoint of cost because an ionization effect by salt has a limit, that is, electrical conduction performance is saturated at 13 wt %.

Though the addition of salt is almost adopted for improving the electrical conduction performance of the gel, there may be cases where an acidic salt, a basic salt and a functional salt are added for an adjustment of a pH as another object. In addition, in providing the gel with medicinal effects, there may be cases where medicinal ingredients having formed salt are added to the hydrogel. Further, in some cases, salt is added for improving a wetting performance and imparting an antibacterial activity to the gel.

As the salt, which can be used in the present invention, there can be used halogenated alkaline metals or halogenated alkaline-earth metals such as sodium halide, potassium halide, magnesium halide, and calcium halide, another metal halides, hypochlorite, chlorites, chlorates, perchlorates, sulfates, nitrates, phosphates and ammonium salts of various metals, inorganic salts such as various complex salts, univalent organic carboxylates such as acetic acid, benzoic acid, lactic acid, and tartaric acid, univalent or bivalent or higher salts of polyvalent carboxylic acids such as phthalic acid, succinic acid, adipic acid, and citric acid, metallic salts and organic ammonium salts of organic acids such as sulfonic acid and amino acid, and salts of polymer electrolytes such as poly(meth)acrylic acid, polyvinylsulfonic acid, polytertialbutylacrylamido sulfonic acid, polyallylamine, polyethylene imine. In addition, even though salt is insoluble in water and in the form of being dispersed in water, it is also possible to disperse the salt in the gel with time. In this case, silicates, aluminates, oxides and hydroxides of metal can be used.

In addition, the amount of water contained in the polymeric hydrogel in the present invention is not specifically limited. Specifically, in a time right after producing the polymeric hydrogel, the water content of the polymeric hydrogel may be larger than, smaller than or equal to a water content of equilibrium. Further, when the polymeric hydrogel is left in the air, it absorbs the moisture in the air or releases water into the air, and its water content reaches equilibrium gradually. Therefore, when its water content is set at a level other than the water content of equilibrium, the polymeric hydrogel is preferably stored in a container through which water does not permeate.

A constitution of the container is not specifically limited and any constitution well known in this field can be employed. For example, bags made of film having a property as a barrier against water can be given. Examples of the constitution of the film include constitutions such as polyester/polyethylene/aluminum foil/polyethylene, polyester/aluminum vapor deposition film/polyethylene, polyester/silica vapor deposition film/polyethylene, and the like, which are laminated in this order from outside. Among the above-mentioned constitutions, the constitution including an aluminum foil is preferred since it has a high property as a barrier against water.

One example of a method of holding the polymeric hydrogel in a bag will be described referring to FIG. 1. First, two sheets of a rectangular film (polyester 1/polyethylene 2/aluminum foil 3/polyethylene 4) having a constitution of a cross section shown in FIG. 1(a) are prepared. Next, by opposing two sheets of a rectangular film to each other with a side of the polyethylene 4 inside and heat-sealing an end portion 6 other than an opening 5 for inserting the polymeric hydrogel, a bag is formed. A polymeric hydrogel 7 is inserted into the resulting bag through the opening 5 (FIG. 1(b)). Then, by heat-sealing the opening 5, the polymeric hydrogel can be held in the bag (FIG. 1(c)).

A production-method of the polymeric hydrogel in the present invention is not specifically limited and any publicly known method can be adopted. For example, the polymeric hydrogel can be obtained by dispersing the nonionic polymerizable monomer and the crosslinking monomer for producing the polymeric matrix in an aqueous medium (water, a mixed medium of water and alcohol, and the like); adding the wetting agent, the solvent and another additives to this dispersion; adding a publicly known polymerization initiator; and crosslinking these mixture through heating or irradiating ultraviolet light. The initiator may be a thermal polymerization initiator or a photopolymerization initiator. It is also possible to impregnate a polymeric matrix previously formed by a polymerization reaction with the wetting agent and the solvent.

For example, a method of using a self-crosslinking polymer copolymer solution described in Japanese Unexamined Patent Publication No. HEI 11(1999)-349786 can be also adopted. Here, the self-crosslinking copolymer solution has an advantage that in producing the polymeric hydrogel, a radical polymerization reaction is not involved and medicinal ingredients can be easily added. On the contrary, a crosslinking reaction is initiated by a desorbed group present in a part of a side chain of a straight-chain polymer, which has been polymerized, and a crosslinking point is produced in a certain probability and all functional groups does not necessarily produce the crosslinking point.

The polymeric hydrogel of the present invention preferably controls the water-absorbing power. As a factor of controlling the water-absorbing power of the polymeric hydrogel, there is given the crosslinking density. Preferably, an addition amount of the crosslinking monomer to form crosslinking points is previously controlled and, after the reaction, the added crosslinking monomer forms crosslinking points with reliability in order to control the crosslinking density. Accordingly, it is preferred, by using the crosslinking monomer having two or more double bonds having a polymerizable property in a molecule and to co-crosslink in a one-step reaction as described above as a suitable example, to co-crosslink monomers at single reaction.

To the polymeric hydrogel in the present invention, an antiseptic, a disinfectant, an antimold agent, a corrosion inhibitor, antioxidant, a stabilizer, a perfume, a surfactant, a coloring matter, and medicinal ingredients such as anti-inflammatory agent, a vitamin preparation, a whitening agent and others may be appropriately added as required. Examples of a method of adding the medicinal ingredients include: a method of previously dissolving or dispersing the medicinal ingredients in a compound solution and forming the polymeric matrix; and a method of adding the medicinal ingredients later to a polymeric hydrogel previously produced. Of these methods, addition of the medicinal ingredients by the latter method is more preferable because there may be cases where in a step of producing the gel involving a radical polymerization reaction, the medicinal ingredients are attacked by radicals to lose medicinal effects.

The polymeric hydrogel of the present invention can be suitably used as materials of bioelectrodes, medical adhesives, coupling materials for ultrasonic measuring, cosmetics, quasi-drugs, electrodes for industrial measurements and industrial adhesives. Particularly, the polymeric hydrogel of the present invention is most preferably used as bioelectrodes and medical adhesives.

EXAMPLES

Hereinafter, the present invention will be described in more detail by way of examples, but the present invention is not limited by these examples.

Example 1

First, acrylamide (M1) and polyethyleneglycol methacrylate (M3) as a nonionic polymerizable monomer, N,N-methylenebisacrylamide (C1) as a cross g monomer, sodium chloride (N) as an electrolytic salt, and polyglycerin (hexamer) (G1) and polyethyleneglycol (G3) as a wetting agent were blended in a blending rate (wt %) shown in Table 1, and to this mixture was added ion-exchanged water as a solvent to form a mixture assumed as 100 wt %, and this mixture was dissolved and stirred to obtain a monomer compound solution.

As the above polyethyleneglycol methacrylate (M3), there was used polyethyleneglycol methacrylate which an "n" in a polyethyleneglycol unit of $—(CH_2CH_2O)_n—$ (n: number of repeating units) is about 2 (n≈2).

Next, to 100 parts by weight of the monomer compound solution was added 0.3 parts by weight of 1-hydroxy-cyclohexylphenyl ketone (trade name IRGACURE 184, produced by Ciba Specialty Chemicals K.K.) as a photopolymerization initiator and the mixture was stirred and dissolved. The blending rates of the respective components forming the monomer compound solution are shown in Table 1. However, the values in Table 1 represent wt % relative to the total amount of a compound solution added with ion-exchange water. The monomer compound solution obtained was adjusted to a temperature of 4° C. and then spread thinly on a polyethylene terephthalate film. Next, a, crosslinking polymerization reaction was initiated by irradiating this monomer compound solution with ultraviolet light having the intensity of 50 mW/cm$^2$ for 60 seconds and a sheet-type tacky polymeric hydrogel having a thickness of 1.0 mm was obtained.

In order to perform an immersion test, a polyester film (weight: W1 [g]), being a supporting member, coated with carbon was bonded to the one side of the resulting gel and the gel supported by the polyester film was cut in a size of 50 mm square to prepare a test piece. Further, by being kept stationary for 24 hours in environments of 23±5° C. in temperature and 55±10% in relative humidity with a gel side up prior to an immersion test, the test piece was brought into a condition of equilibrium of a water content and then used for the immersion.

(1) Increase in the Weight of Gel in Immersion of the Period of 5 Minutes 50 g of ion-exchanged water weighed was put in a box-type plastic petri dish of 100 mm in length, 100 mm in width and 20 mm in depth. The test piece, weight (W2 [g]) of which was previously measured, was immersed in the ion-exchanged water, and after a lapse of 5 minutes, it was taken out from the petri dish and drained gently on at an edge of the petri dish to remove water droplets on the surfaces of the gel and the supporting member, and then the weight (W3 [g]) of the test piece was measured. Here, the remaining water drained into the petri dish was used as an eluate for an evaluation of the amount of elution in immersion of the period of 5 minutes. The increase in the weight of gel in immersion was determined from Equation 2. The result is shown in Table 3.

$$\text{Increase in the weight in immersion of the period of 5 minutes (wt \%)} = (W3-W2)/(W2-W1) \times 100 \quad \text{Equation 2}$$

(2) Amount of Elution of Gel in Immersion of the Period of 5 Minutes

The eluate obtained in an evaluation of the increase in the weight in immersion of the period of 5 minutes was transferred from the petri dish to a glass container, weight (W4 [g]) of which was previously measured, and the inside of the petri dish was washed twice with ion-exchanged water and the ion-exchanged water used for water washing was added to the eluate in the glass container. Next, the glass container was dried for 16 hours in an oven controlled to 105° C. to evaporate the water content of the eluate to dryness and then cooled to room temperature over 30 minutes in a desiccator containing silica gel, and then the weight (W5 [g]) of the glass container containing the eluate was measured. Amount of elution of gel was determined from Equation 3. The result is shown in Table 3.

$$\text{Amount of elution in immersion of the period of 5 minutes (wt \%)} = (W5-W4)/(W2-W1) \times 100 \quad \text{Equation 3}$$

Example 2

A polymeric hydrogel was obtained by following the same procedure as that of Example 1 except that acrylamide (M1) and N,N-dimethylacrylamide (M2) as the nonionic polymerizable monomer, N,N-methylenebisacrylamide (C1) and polyethyleneglycol dimethacrylate (C2) as the crosslinking monomer, sodium chloride (N) as the electrolytic salt, and polyglycerin (hexamer) (G1), polyglycerin (decamer) (G2) and polyethyleneglycol (G3) as the wetting agent were blended in a blending rate (wt %) shown in Table 1. The obtained polymeric hydrogel was subjected to an immersion test by following the same procedure as that of Example 1 and its results are shown in Table 3. Here, as the above polyethyleneglycol dimethacrylate (C2), there was used polyethyleneglycol dimethacrylate which an "n" in a polyethyleneglycol unit of —$(CH_2CH_2O)_n$— (n: number of repeating units) is about 4 (n≈4).

Example 3

A polymeric hydrogel was obtained by following the same procedure as that of Example 1 except that acrylamide (Ml) as the nonionic polymerizable monomer, N,N-methylenebisacrylamide (C1) as the crosslinking monomer, sodium chloride (N) as the electrolytic salt, and polyglycerin (hexamer) (G1), polyglycerin (decamer) (G2) and glycerin (G6) as the wetting agent were blended in a blending rate (wt %) shown in Table 1. The obtained polymeric hydrogel was subjected to an immersion test by following the same procedure as that of Example 1 and its results are shown in Table 3.

Further, a cycling test and its evaluation were conducted by using the following procedure to determine a correlation between an increase in the weight of gel/the amount of elution of gel in immersion of the period of 5 minutes and those in actual use.

(3) Cycling Test and its Evaluation

After the test piece, weight (W2) of which was previously measured, was immersed in about 2 L of running water put into a 3 L beaker for 10 minutes, it was drained well and put on a paper towel with the face of a supporting member down to remove remaining water droplets, and the weight ($W6_n$) was measured. Next, this test piece was kept stationary with a gel side up in an oven controlled to 60° C. and taken out from the oven 10 minutes later. The test piece was kept stationary for 24 hours with a gel side up similarly in environments of 23±5° C. in temperature and 55±10% in relative humidity and then its weight ($W7_n$) was measured. By repeating this procedure 20 times, the weights ($W6_1$) to ($W6_{20}$) and ($W7_1$) to ($W7_{20}$) were measured. Further, a change in the weight after water washing (wt %) and a change in the weight after drying (wt %) were determined from Equation 4 and Equation 5, respectively. The change in the weight after water washing is shown in Table 4 and FIG. 2, and the change in the weight after drying is shown in Table 5 and FIG. 3.

$$\text{Change in the weight after water washing (wt \%)} = (W_{6n}-W_1)/(W_2-W_1) \times 100 \quad \text{Equation 4}$$

$$\text{Change in the weight after drying (wt \%)} = (W_{7n}-W_1)/(W_2-W_1) \times 100 \quad \text{Equation 5}$$

Example 4

A polymeric hydrogel was obtained by following the same procedure as that of Example 1 except that acrylamide (M1) and N,N-dimethylacrylamide (M2) as the nonionic polymerizable monomer, N,N-methylenebisacrylamide (C1) as the crosslinking monomer, sodium chloride (N) as the electrolytic salt, and polyglycerin (hexamer) (G1) and polyglycerin (decamer) (G2) as the wetting agent were blended in a blending rate (wt %) shown in Table 1. The obtained polymeric hydrogel was subjected to an immersion test by following the same procedure as that of Example 1 and its results are shown in Table 3. Further, (3) an cycling test and its evaluation was conducted by following the same procedure as that of Example 3, and its results are shown in Table 4 and FIG. 2, and Table 5 and FIG. 3.

Example 5

A polymeric hydrogel was obtained by following the same procedure as that of Example 1 except that N,N-dimethylacrylamide (M2) as the nonionic poly-merizable monomer, N,N-methylenebisacrylamide (C1) as the crosslinking monomer, sodium chloride (N) as the electrolytic salt, and polyglycerin (hexamer) (G1) as the wetting agent were blended in a blending rate (wt %) shown in Table 1. The obtained polymeric hydrogel was subjected to an immersion test by following the same procedure as that of Example 1 and its results are shown in Table 3.

Example 6

A polymeric hydrogel was obtained by following the same procedure as that of Example 1 except that polypropyleneglycol acrylate (M4) as the nonionic polymerizable monomer, polyethyleneglycol (n≈4) dimethacrylate (C2) as the crosslinking monomer, and polyoxyethylenediglycerin (average molecular weight: 948) (G4) as the wetting agent were blended in a blending rate (wt %) shown in Table 1. The obtained polymeric hydrogel was subjected to an immersion test by following the same procedure as that of Example 1 and its results are shown in Table 3. Here, as the above polypropyleneglycol acrylate (M4), there was used polypropyleneglycol acrylate which an "n" in a polypropyleneglycol unit of —$(CH_2CH(CH_3)O)_n$— (n: number of repeating units) is about 6 (n≈6).

Example 7

A polymeric hydrogel was obtained by following the same procedure as that of Example 1 except that polypropyleneglycol (n≈6) acrylate (M4) as the nonionic polymerizable monomer, polyethyleneglycol (n≈4) dimethacrylate (C2) as the crosslinking monomer, and polyoxyethylene sorbit (average molecular weight: 2563) (G5) as the wetting agent were blended in a blending rate (wt %) shown in Table 1. The obtained polymeric hydrogel was subjected to an immersion test by following the same procedure: as that of Example 1, and its results are shown in Table 3.

Comparative Example 1

Acrylamide (M1) as a polymerizable monomer, N,N-methylenebisacrylamide (C1) as the crosslinking monomer, sodium chloride (N) as the electrolytic salt, and glycerin (G6) as the wetting agent were blended in a blending rate (wt %) shown in Table 1, and to this mixture was added ion-exchanged water as a solvent to form a mixture assumed as 100 wt %, and this mixture was dissolved and stirred to obtain a monomer compound solution.

Next, to 100 parts by weight of the monomer compound solution was added 0.3 parts by weight of 1-hydroxy-cyclohexylphenyl ketone (trade name IRGACURE 184, produced by Ciba Specialty Chemicals K.K.) as a photopolymerization initiator and the mixture was stirred and dissolved. The blending rates of the respective components forming the monomer compound solution are shown in Table 1. However, the values in Table 1 represent wt % relative to the total amount of a compound solution added with ion-exchange water. The monomer compound solution obtained was adjusted to a temperature of 4° C. and then spread thinly on a polyethylene terephthalate film. Next, a crosslinking polymerization reaction was initiated by irradiating this monomer compound solution with ultraviolet light having the intensity of 50 mW/cm$^2$ for 60 seconds.

The obtained sample was processed into a test piece under conditions similar to Example 1, and (1) an increase in the weight of gel and (2) the amount of elution of gel in immersion of the period of 5 minutes were evaluated. The results are shown in Table 3.

Further, (3) cycling test and its evaluation was conducted by following the same procedure as that of Example 3. The results are shown in Table 4 and FIG. 2, and Table 5 and FIG. 3.

Comparative Example 2

A polymeric hydrogel was obtained by following the same procedure as that of Example 1 except that acrylamide (M1) as the polymerizable monomer, N,N-methylenebisacrylamide (C1) as the crosslinking monomer, sodium chloride (N) as the electrolytic salt, and polyethyleneglycol (G3) and glycerin (G6) as the wetting agent were blended in a blending rate (wt %) shown in Table 1. The obtained polymeric hydrogel was subjected to an immersion test by following the same procedure as that of Example 1 and its results are shown in Table 3.

Further, (3) a cycling test and its evaluation was conducted by following the same procedure as that of Example 3. The results are shown in Table 4 and FIG. 2, and Table 5 and FIG. 3.

Comparative Example 3

A polymeric hydrogel was obtained by following the same procedure as that of Example 1 except that acrylamide (M1) as the polymerizable monomer, N,N-methylenebisacrylamide (C1) as the crosslinking monomer, sodium chloride (N %) as the electrolytic salt, and polyethyleneglycol (G3) as the wetting agent were blended in a blending rate (wt %) shown in Table 1. The obtained polymeric hydrogel was subjected to an immersion test by following the same procedure as that of Example 1 and its results are shown in Table 3.

Comparative Example 4

Sodium polyacrylate (molecular weight: about 5,000,000) (M5) and polyacrylic acid (molecular weight: about 300,000) (M6), glycerin (G6) and 1,3-butanediol (G7) were blended in a blending rate (wt %) shown in Table 1 and mixed, and to this mixture was further added ion-exchanged water and the resulting mixture was kneaded at 50° C. for about 30 minutes for uniformity. Further, ion-exchanged water was added in such a manner that the total of compounds M5, M6, G6, G7 and synthesized aluminum silicate C to be added later and ion-exchanged water is 100 wt %.

Next, synthesized aluminum silicate (C) was added in a blending rate of Table 1 as a crosslinking factor and the mixture was further kneaded at 60° C. for 10 minutes for uniformity. The compound solution obtained thus was spread on a polyethylene terephthalate film by using a doctor blade and then allowed to stand at room temperature for about 2 hours, thereby obtaining a sheet-type gel having a thickness of 1.0 mm. The composition of the sample is shown in Table 1.

The obtained sample was processed into a test piece under conditions similar to Example 1, and (1) an increase in the weight of gel and (2) the amount of elution of gel in immersion of the period of 5 minutes were evaluated. The results are shown in Table 3.

Though an effort was made to conduct the cycling test on Comparative Example 4, a gel was peeled off from a supporting member because of weak adhesion between the gel and the supporting member when contacted with ion-exchanged water; therefore, the sample was considered not to withstand the cycling test.

TABLE 1

| | Polymerizable monomer | | | | | | Crosslinking Monomer | | | Electrolytic salt | Wetting agent | | | | | | | Water |
|---|---|---|---|---|---|---|---|---|---|---|---|---|---|---|---|---|---|---|
| | M1 | M2 | M3 | M4 | M5 | M6 | C1 | C2 | C | N | G1 | G2 | G3 | G4 | G5 | G6 | G7 | |
| Examples | | | | | | | | | | | | | | | | | | |
| 1 | 18 | — | 2 | — | — | — | 0.06 | — | — | 2 | 50 | 10 | — | — | — | — | — | 17.94 |
| 2 | 15 | 5 | — | — | — | — | 0.05 | 0.05 | — | 2 | 40 | 10 | 10 | — | — | — | — | 17.9 |
| 3 | 20 | — | — | — | — | — | 0.1 | — | — | 2 | 40 | 10 | — | — | — | 10 | — | 17.9 |
| 4 | 10 | 10 | — | — | — | — | 0.08 | — | — | 3 | 30 | 30 | — | — | — | — | — | 16.92 |
| 5 | — | 20 | — | — | — | — | 0.1 | — | — | 5 | 55 | — | — | — | — | — | — | 19.9 |

TABLE 1-continued

| | Polymerizable monomer | | | | | | Crosslinking Monomer | | | Electrolytic salt | Wetting agent | | | | | | | |
|---|---|---|---|---|---|---|---|---|---|---|---|---|---|---|---|---|---|---|
| | M1 | M2 | M3 | M4 | M5 | M6 | C1 | C2 | C | N | G1 | G2 | G3 | G4 | G5 | G6 | G7 | Water |
| 6 | — | — | — | 30 | — | — | 0.3 | — | — | — | — | — | — | 55 | — | — | — | 14.7 |
| 7 | — | — | — | 30 | — | — | 0.3 | — | — | — | — | — | — | — | 55 | — | — | 14.7 |
| Comparative Examples | | | | | | | | | | | | | | | | | | |
| 1 | 20 | — | — | — | — | — | 0.05 | — | — | 2 | — | — | — | — | — | 60 | — | 17.95 |
| 2 | 20 | — | — | — | — | — | 0.06 | — | — | 2 | — | — | 18 | — | — | 42 | — | 17.94 |
| 3 | 20 | — | — | — | — | — | 0.06 | — | — | 2 | — | — | 60 | — | — | — | — | 17.94 |
| 4 | — | — | — | — | 2 | 8 | — | — | 1.5 | — | — | — | — | — | — | 5 | 10 | 73.5 |

Values in the above table is represented by wt %.

TABLE 2

| | G1 | G2 | G3 | G4 | G5 | G6 | G7 |
|---|---|---|---|---|---|---|---|
| | | | Polymer | | | | Monomer |
| Average molecular weight | 500 | 750 | 400 | 948 | 2563 | 92 | 90 |
| (Number of ether groups + number of hydroxyl groups)/number of carbon atoms in polymer | About 13/18 ≈ 2/3 | About 21/30 ≈ 2/3 | About 10/18 ≈ 1.7/3 | About 19/48 ≈ 1.2/3 | About 47/129 ≈ 1.1/3 | 1 | 1/2 |
| Number of hydroxyl groups in a molecule | 8 | 12 | 2 | 4 | 6 | 3 | 2 |

TABLE 3

| | Increase in the weight in immersion of the period of 5 minutes | Amount of elution |
|---|---|---|
| Example 1 | 30 | 5.9 |
| Example 2 | 36 | 5.7 |
| Example 3 | 30 | 6.7 |
| Example 4 | 38 | 5.5 |
| Example 5 | 27 | 6.2 |
| Example 6 | 8 | 4.2 |
| Example 7 | 5 | 1.2 |
| Comparative Example 1 | 47 | 13 |
| Comparative Example 2 | 65 | 12 |
| Comparative Example 3 | 72 | 9.7 |
| Comparative Example 4 | 460 | 3.7 |

TABLE 4

| | Before measurement | After 5 cycles | After 10 cycles | After 15 cycles | After 20 cycles |
|---|---|---|---|---|---|
| Example 3 | 100 | 106 | 103 | 98 | 92 |
| Example 4 | 100 | 109 | 107 | 99 | 98 |
| Comparative Example 1 | 100 | 102 | 91 | 79 | 67 |
| Comparative Example 2 | 100 | 104 | 94 | 85 | 77 |

TABLE 5

| | Before measurement | After 5 cycles | After 10 cycles | After 15 cycles | After 20 cycles |
|---|---|---|---|---|---|
| Example 3 | 100 | 97 | 93 | 88 | 81 |
| Example 4 | 100 | 100 | 97 | 91 | 89 |
| Comparative Example 1 | 100 | 91 | 79 | 67 | 55 |
| Comparative Example 2 | 100 | 93 | 83 | 75 | 67 |

From Table 3, it is shown that in Examples 1 to 7, in immersion of the period of 5 minutes, any increase in the weight of gel was 50 wt % or less and any amount of elution of gel was 10 wt % or less. On the contrary, in Comparative Example 2, in immersion of the period of 5 minutes, the increase in the weight exceeded 50 wt % and, also, the amount of elution exceeded 10 wt %. In Comparative Example 1, in immersion of the period of 5 minutes, the increase in the weight was 50 wt % or less but the amount of elution exceeded 10 wt %. Further, in Comparative Examples 3 and 4, in immersion of the period of 5 minutes, the amounts of elution were 10 wt % or less but the increase in the weight exceeded 50 wt %.

Figure 2:
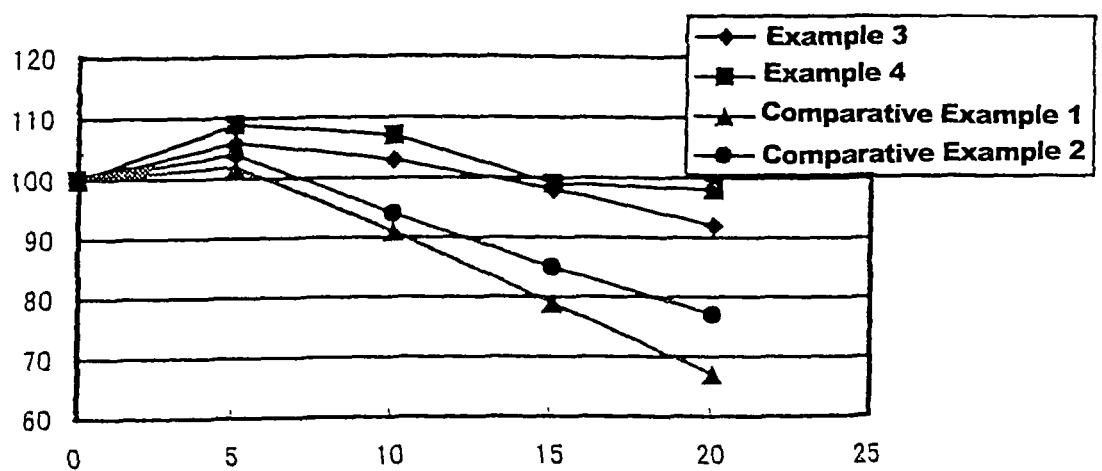
FIG. 2 is a graph showing a relation between a number of water washing of a gel and change in the weight after water washing in the examples 3 and 4, and comparative examples 1 and 2.

From Table 4 and FIG. 2, it is shown that the weights of gel immediately after washing of 20 cycles were significantly reduced to 67% and 77% of the initial weights in Comparative Examples and, on the other hand, the reductions of the weights fell within 10% of the initial weights in Examples. In addition, thicknesses of gels did not decrease so much compared with the initial thicknesses except for Comparative Example 1.

Figure 3:
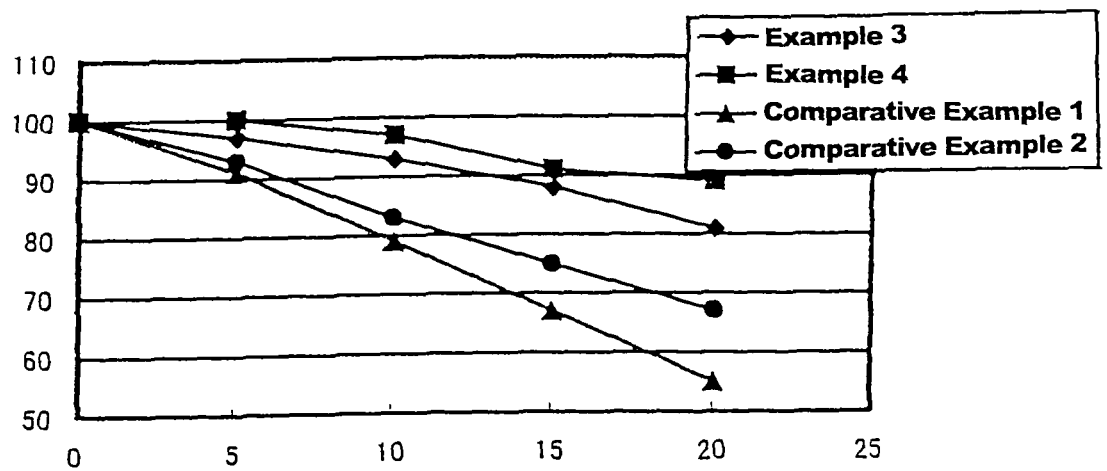
FIG. 3 is a graph showing a relation between a number of water washing of a gel and change in the weight after water washing and drying in the examples 3 and 4, and comparative examples 1 and 2.

It is apparent from Table 5 and FIG. 3 that when drying was conducted after washing, Examples kept 80% to 90% of the initial weights but Comparative Examples decreased to 55% and 67% of the initial weights by a large amount. This means that in the weight immediately after washing, the decrease in the weight of the gel became small apparently since gels held water but the weight of the gel in a condition of equilibrium actually decreased since the wetting agent in the gel was eluted as shown in Table 3.

Further, it is shown from Table 5 and FIG. 3 that even though Comparative Examples 1 and 2 have less increase in the weights in immersion of the period of 5 minutes than Examples 3 and 4, the weights after washing in 5 cycles and 10 cycles of the cycling test were reversed. The reason for this becomes clear by comparing it with the weight after drying. In 5 cycles of the cycling test, the gels of the comparative examples have been already reduced in the weight by almost 10 wt % due to the elution of gel and the comparative examples have more amount of water absorbed relative to the substantial weights of gel at this point in time than the examples.

The polymeric hydrogel of the present invention has high water resistance. Therefore, when the polymeric hydrogel of the present invention is adopted particularly in gel pads and bioelectrodes, it is possible to water-wash it repeatedly and, also, in the case of water washing for several seconds, it is possible to prolong its life since the wetting agent in the gel is resistant to be eluted even in water washing repeatedly. Further, when it is used for a living body, it becomes a good biological sticking material having less deterioration due to contact with sweat even in the case of sweating heavily. Further, when it is used in industrial measurements for use outdoors, it becomes possible to prolong the life compared with the conventional gel since it has great resistance to environments.

What is claimed is:

1. A polymeric hydrogel comprising a polymeric matrix formed by copolymerizing a nonionic polymerizable monomer with a crosslinking monomer, wherein the polymeric matrix contains a wetting agent and water, at least 50 wt % of the wetting agent is constituted of a polymer chosen from polyglycerin having 8 to 12 hydroxyl groups, and the polymer is water-soluble and has an average molecular weight of 150 to 4000 and satisfies the relationship: {(number of ether groups in the polymer+number of hydroxyl groups in the polymer)/number of carbon atoms present in the polymer}≧1/3, wherein the nonionic polymerizable monomer is selected from acrylamide, polyethyleneglycol methacrylate, N,N-dimethylacrylamide, and polypropyleneglycol acrylate, wherein the crosslinking monomer is selected from N,N-methylenebisacrylamide and polyethyleneglycol dimethacrylate.

2. The polymeric hydrogel according to claim 1, wherein the polymeric hydrogel contains 5 to 50 wt % water.

3. The polymeric hydrogel according to claim 1, wherein the polymeric hydrogel comprises up to 13% dissolved electrolyte.

4. The polymeric hydrogel according to claim 1, wherein the polymeric hydrogel is used as a bioelectrode or medical adhesive.

5. The polymeric hydrogel according to claim 1, wherein the polyglycerin comprises a polyglycerin having 8 hydroxyl groups.

6. The polymeric hydrogel according to claim 1, wherein the polyglycerin comprises a polyglycerin having 12 hydroxyl groups.

7. The polymeric hydrogel according to claim 1, wherein the polymer is water-soluble and has an average molecular weight of 500 to 750.

* * * * *

UNITED STATES PATENT AND TRADEMARK OFFICE
CERTIFICATE OF CORRECTION

PATENT NO. : 8,541,020 B2
APPLICATION NO. : 10/485829
DATED : September 24, 2013
INVENTOR(S) : S. Sasahara et al.

It is certified that error appears in the above-identified patent and that said Letters Patent is hereby corrected as shown below:

On the Title Page, Item 73, Assignee, please change "Seikisui" to --Sekisui--.

Signed and Sealed this
Fourteenth Day of January, 2014

Michelle K. Lee
*Deputy Director of the United States Patent and Trademark Office*